United States Patent [19]

Klein

[11] 4,226,589
[45] Oct. 7, 1980

[54] ORTHODONTIC HEADGEAR RELEASE ASSEMBLY

[76] Inventor: Paul E. Klein, 601 First St., Lake Oswego, Oreg. 97034

[21] Appl. No.: 827,727

[22] Filed: Aug. 25, 1977

[51] Int. Cl.³ .............................................. A61C 7/00
[52] U.S. Cl. .................................. 433/5; 24/201 TR
[58] Field of Search .................. 24/115 F, 201 TR; 32/14 D; 114/217

[56] References Cited

U.S. PATENT DOCUMENTS

| | | | |
|---|---|---|---|
| 1,752,619 | 4/1930 | Summerfeld | 24/115 F |
| 2,452,796 | 11/1948 | Skibsted | 24/115 F |
| 2,518,179 | 8/1950 | Quinby et al. | 24/115 F |
| 2,940,622 | 6/1960 | Kays | 24/201 TR |
| 3,439,387 | 4/1969 | Churches | 24/201TR |
| 3,686,757 | 8/1972 | McVickers et al. | 32/14 D |
| 4,115,921 | 9/1978 | Armstrong | 32/14 D |

Primary Examiner—Louis G. Mancene
Assistant Examiner—Michael J. Foycik, Jr.
Attorney, Agent, or Firm—Kolisch, Hartwell & Dickinson

[57] ABSTRACT

Safety-release tension-applying mechanism for use between an orthodontic facebow and a headstrap and the like therefor. The mechanism includes a pair of releaseably interengageable portions which, while engaged, are smoothly elastically shiftable relative to one another throughout a preselected tension range. These portions automatically release on the tension transmitted through the mechanism exceeding a predetermined maximum tension level.

2 Claims, 12 Drawing Figures

ORTHODONTIC HEADGEAR RELEASE ASSEMBLY

BACKGROUND AND SUMMARY OF THE INVENTION

This invention pertains to orthodontic headgear, and more particularly to a safety-release tension-applying mechanism for use between an orthodontic facebow and a headstrap and the like therefor.

It is common in certain orthodonture practices to use what is known as a facebow for applying certain tooth-positioning and/or mouth-positioning forces. The usual facebow includes an inner bow which seats in tubes, or other suitable devices, mounted on bands which have been attached to a patient's teeth, and an outer bow which is attached to the inner bow, and which extends around the opposite sides of the patient'face. Tension is applied, ordinarily, through an elastic neckstrap or headstrap, or the like, whose opposite ends hook with the opposite ends of the outer bow in a facebow.

There have been a number of incidents in the past where, either accidentally or intentionally, a facebow is pulled forwardly away from a patient's face and then released. This situation produces a very dangerous slingshot effect when the facebow shoots back at a patient's face. Serious accidents, including blinding, have occurred in recent years.

A general object of the present invention is to provide a unique safety-release tension-applying mechanism adapted to be interpositioned between such a facebow and a headstrap or the like, and constructed to release the connection between these two devices under circumstances with the facebow pulled just a slight distance away from a patient's face.

Still another object of the invention is to provide such a mechanism which, while capable of releasing the connection between a facebow and a headstrap, etc., it is also capable of transmitting the desired normal range of orthodontic tension without releasing the connection.

A further object of the instant invention is to provide a mechanism of the type so far generally described which is not easily defeated or disabled by a patient, and which, when release occurs, is easily reassembled with a return to the proper orthodontic force.

According to a preferred embodiment of the invention, the proposed safety-release mechanism includes a pair of releasably interconnectable parts, one of which includes a pair of spaced opposed relatively movable fingers which act as an infinitely changeable tension-producing gripper, and the other of which includes a portion shaped releasably to be gripped by this gripper. As tension is transmitted through the mechanism increases, the two parts just mentioned therein tend to shift apart from one another, with gradual spreading of the fingers in the first mentioned part. Such fingers, therefore, function as active tension-applying elements in an overall assembly including a headstrap and the like and an orthodontic facebow. The parts in the mechanism continue to move apart with increased tension, as for example might be caused by someone pulling outwardly on a face bow, throughout a prescribed predetermined range of tensions, whereupon the two parts in the mechanism automatically and smoothly release. Nothing is built into the mechanism which tends to stop the gradual and progressive separation of the parts as such tension buildup occurs.

Another feature of the invention is that the two parts are constructed to engage in such a manner as to allow for relative rotation or pivoting about an axis substantially normal to that axis along which tension may be transmitted. This is an important feature in maximizing wearer comfort since it allows angulation to occur between a facebow and a headstrap so as to place both in the most advantageous and comfortable positions.

In most instances, a pair of mechanisms constructed in accordance with the invention will preferably be used, each being operatively interconnected between an end of a facebow and an end of a headstrap or the like. However, it is recognized that there are some applications in which but a single mechanism might be entirely satisfactory. Also, two different modifications of the invention, differing slightly in construction, are shown and described specifically herein. Other modifications are suggested by way of description.

As will become apparent from the description which follows, if a releasing action takes place, it is an extremely simple matter for a patient to reassemble the mechanism. Further, reassembly results in substantially exactly the same orthodontic force existing in the overall headgear as existed prior to release. Further, the modifications of the invention described herein are not placeable into use without the safety-release feature being automatically operative. In other words, it is not practically possible for a patient to defeat the safety-release feature.

As will also be explained below, the sizing of various parts used in the mechanism of the invention is a matter of choice, and can be used as a means for controlling the specific range of orthodontic tension forces which an orthodontist wishes to use. Thus, a relatively wide range of normal orthodontic forces may be applied through the mechanism. These and other objects and advantages attained by the invention will become more fully apparent as the description which now follows is read in conjunction with the accompanying drawings.

DETAILED DESCRIPTION OF THE INVENTION

Figure 1:
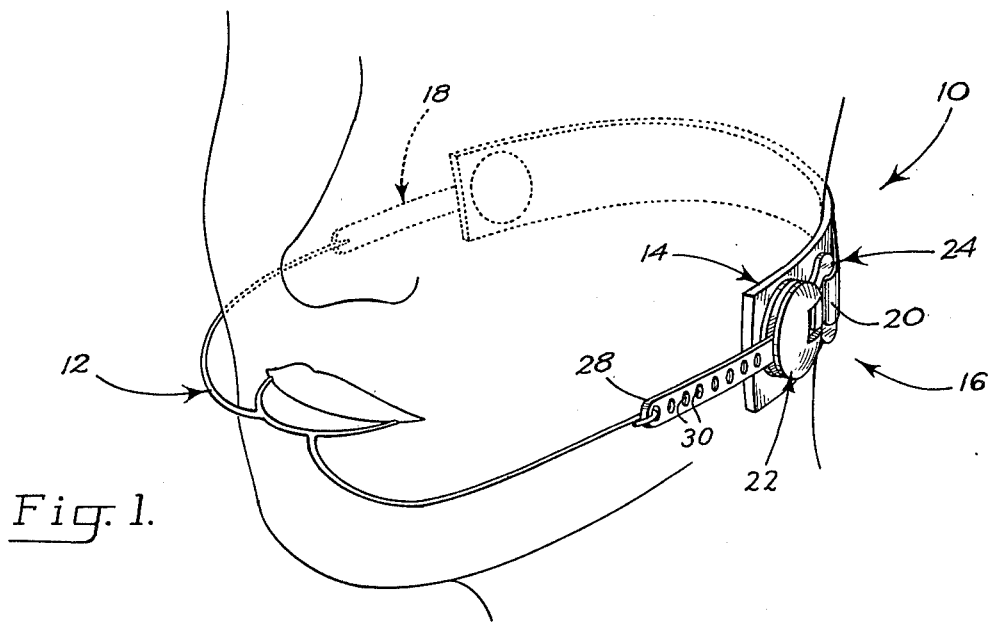
FIG. 1 is a simplified top perspective view showing a patient wearing orthodontic headgear which employs a pair of safety-release mechanisms constructed in accordance with the present invention.

Turning now to the drawings, and referring first to FIG. 1, indicated generally at 10 is an orthodontic headgear properly positioned for use on a patient's head. Headgear 10 includes a conventional facebow 12 whose outer ends extend along the opposite side of the patient's face, and a conventional flexible nonelastic neckstrap 14. Indicated generally at 16, 18 in FIG. 1 are two identical safety-release tension-applying mechanisms constructed in accordance with the present invention which mechanism interconnect the opposite outer ends of the facebow with attaching loops, such as loop 20 that are fastened to the back side, and adjacent the opposite ends, of the neckstrap.

As will be more fully explained shortly, a proper amount of tension, as determined by an orthodontist, is transmitted through mechanisms 16, 18 to apply the desired orthodontic force through facebow 12. Mechanisms 16, 18, in fact, allow this amount of tension to be selected within a predetermined range of tensions. However, and as will also be more fully discussed, in the event that the facebow is pulled forwardly away from the wearer's face, the amount of tension transmitted through the safety-release mechanisms reaches the maximum tension level which they are capable of transmitting, and on this occurring, one or both of the mechanisms release the connection between the facebow and the neckstrap, so that no slingshot effect can occur.

Figure 4:
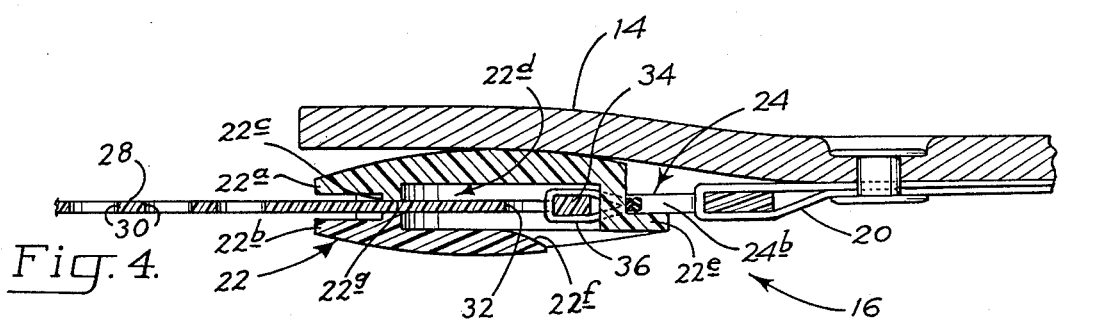
FIG. 4 is a cross-sectional view taken generally along the line 4—4 in FIG. 2.
Figure 3:
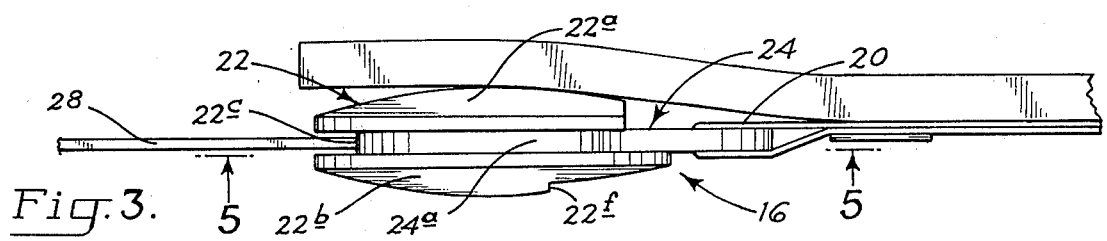
FIG. 3 is a view taken from the top side of FIG. 2.
Figure 2:
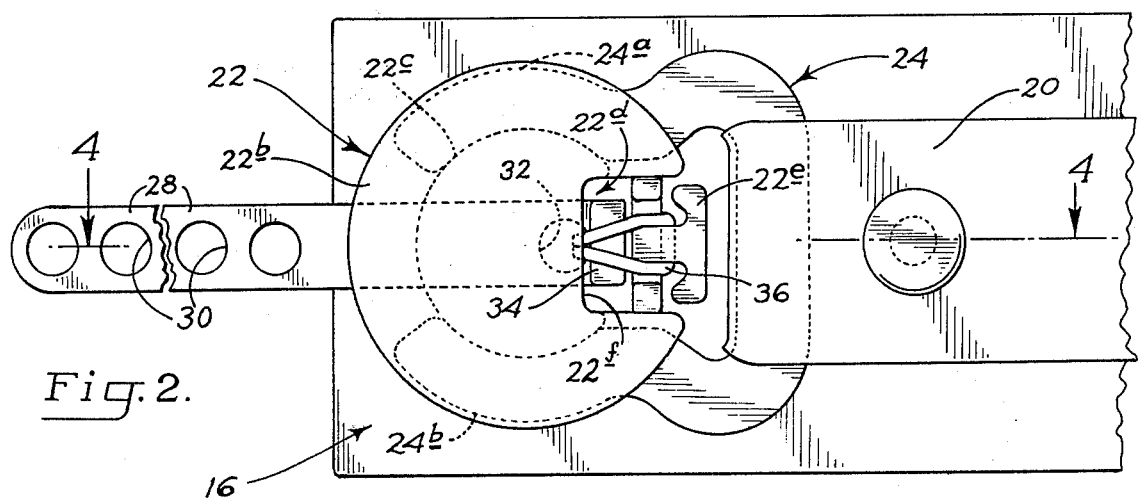
FIG. 2 is an enlarged fragmentary side elevation illustrating details of construction of one of the safety-release mechanism used in the headgear of FIG. 1.

FIGS. 2, 3 and 4 show details of construction of mechanism 16. Referring to these three figures, included in mechanism 16 are what are referred to herein as first and second mechanism parts, or means, 22, 24, respectively. Part 22, also constituting a body unit, takes the form generally of a flatened, cylindrical, button-like wafer whose opposite faces are somewhat domed. Wafer 22 may be formed in any suitable manner, preferably from a lightweight material such as a plastic material. Wafer 22 herein is formed of such a material, and includes a pair of halves 22a, 22b which are appropriately joined along the central radial plane in the wafer. Halves 22a, 22b, when assembled as shown, define a flanged hub 22c (see particularly FIG. 2) having an outer convex circular surface of revolution which extends the better part of a full circle. This outer surface of hub 22c is referred to herein also both as an attaching portion and as a second attaching portion. The upper and lower halves of the circular surface of hub 24c are referred to herein as gripping-surface portions. Defined between halves 22a, 22b, and within the hub, is a generally rectangular void space 22d. Wafer half 22a is formed with a generally T-shaped projecting tab or first attaching means, 22e (see particularly FIGS. 2 and 4). Tab 22e is exposed on the outside of the wafer through a notch 22f which is formed in wafer half 22b.

While the exact dimensions of wafer 22 are not critical, it has been found convenient to form the wafer with an outside diameter generally of about three centimeters, and with the depth of void space 22d being about two centimeters, or perhaps slightly less.

Part 24, which is also referred to herein as a second mechanism part or means, and as a second tensioning means, is preferably formed from a suitable resilient plastic material, and has the configuration most clearly illustrated in FIG. 2. One might think of part 24 as having a somewhat distorted horseshoe-shaped configuration including a pair of opposed spaced arms 24a, and a base 24b. Arms 24a, also referred to as relatively movable elements, and also collectively as a tension-producing portion, are intended by virtue of their inside curved surface-of-revolution faces, releaseably to grip the outside surface of hub 22c. The opposing concave faces in arms 24a are referred to herein as gripping-surface portions. The arms are shown in FIGS. 2, 3 and 4 in positions so gripping the hub. These positions are referred to also herein as normal, relaxed relative positions for the arms. Mechanism part 24 is attached to neckstrap 14 through previously mentioned loop 20, which loop is affixed to the neckstrap through a rivet 26.

Used in conjunction with mechanism 16 is an elongated plastic connector web 28 which includes longitudinally distributed holes, such as those shown at 30, and which projects forwardly from mechanism 16. The inner end of web 28, which is the right end thereof in FIGS. 2, 3 and 4, is provided with an aperture 32 and an enlargement 34. The forward portion of the web extends through a slot 22g provided in hub 22c—the web being insertable to occupy the position shown relative to wafer 22 through insertion of its front end into void space 22d through notch 22f. Enlargement 34 prevents forward retraction of the web from wafer 22. Holes 30 in web 28 accommodate releaseable attachment to the rear hooked ends of facebow 12. This is illustrated in FIG. 1. Naturally, the fact that a web 28 includes a plurality of such holes, enables selective attachment to a facebow at different longitudinal positions along the web. Attaching the inner or right end of web 28 in the figures to mechanism 16 is an endless elastic band 36 first tensioning means, which extends through aperture 32 and hooks twice to tab 22e as shown.

As has previously been mentioned, mechanism 18 is substantially identical in construction to mechanism 16.

Figures 5, 6:
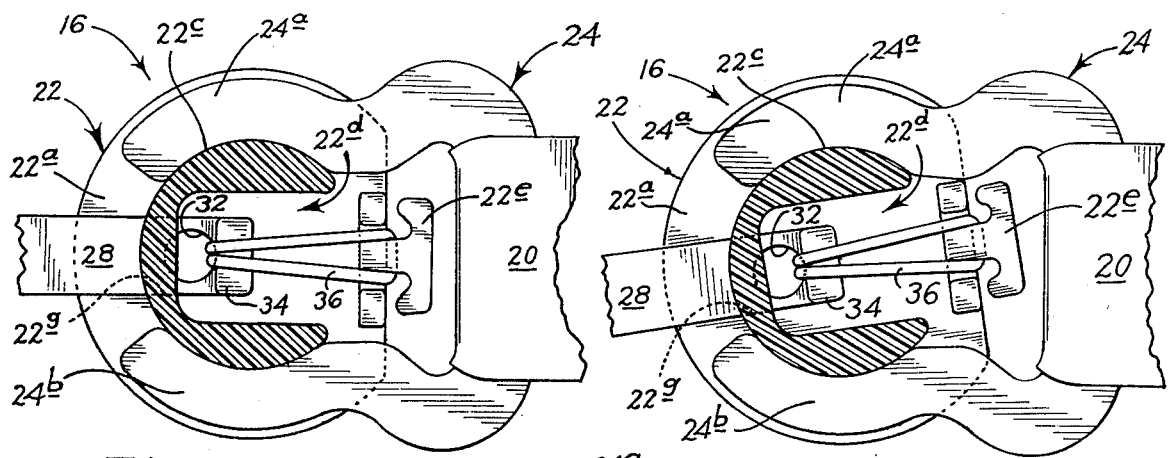
FIG. 5 is a cross-sectional view taken generally along the line 5—5 in FIG. 3.
FIG. 6 is similar to FIG. 5, and illustrates relative rotation which is possible between certain parts of a mechanism constructed according to the invention.

Considering now how the safety-release mechanism of the invention so far described is used and operates, an orthodontist selects the weight of elastic band 36 which he wishes to use between tab 22e and the inner end of a connector web, such as web 28. It is through tension developed in this band, basically, that the level of orthodontic force exerted through the facebow is determined. Obviously, by selecting bands of different sizes or thicknesses, he can control the force level. The orthodontist also selects to which of holes 30 in each web 28 the outer ends of the facebow are to be attached. Through these choices, and with the overall apparatus mounted in place as shown in FIG. 1, the orthodontist sets the appropriate force level. Obviously, mechanism parts 22, 24 are initially engaged as shown in FIGS. 2, 3 and 4. It should be noted, however, that in FIGS. 2, 3 and 4, there is very little stretch shown in band 36, and as a consequence, this is not the normal set of relative positions that exist between mechanisms 22, 24 and the inner end of a web 28 with the apparatus mounted for use on a wearer. Rather, FIG. 5 depicts a typical situation in which there is considerable stretch in band 36, and this drawing thus generally illustrates a normal force-applying condition in the assembled apparatus. It will be noted that the inner end of web 38 is allowed a considerable degree of limited travel within void space 22d, and this range of travel, with a particular selected elastic band, defines the principal operative tension or force range produceable in the overall apparatus.

In FIG. 1, the facebow is shown attached through the mechanisms of the invention to a neckstrap which lies substantially in the same plane as the face bow. Under here circumstances, the longitudinal axes of the neck trap and of web 38 are substantially coplanar. One of the important features of the present invention is that it allows for pivoting or relative angulation between parts 22, 24 to accommodate situations in which there may be some angular difference between the plane containing the facebow and that containing, say, a neckstrap. FIG. 6 illustrates this situation wherein, as compared with FIG. 5, it is easy to see that a slight amount of angulation exists between the parts just mentioned. In other circumstances, orthodontists will use headstraps which rise upwardly from the outer ends of the facebow, and in this situation angulation in a reverse direction from that shown in FIG. 6 is accommodated by mechanism parts 22, 24. It will be noted that arms 24a, 24b simply rotate through sliding contact their positions on hub 22c to accommodate such angulation.

Figure 7:
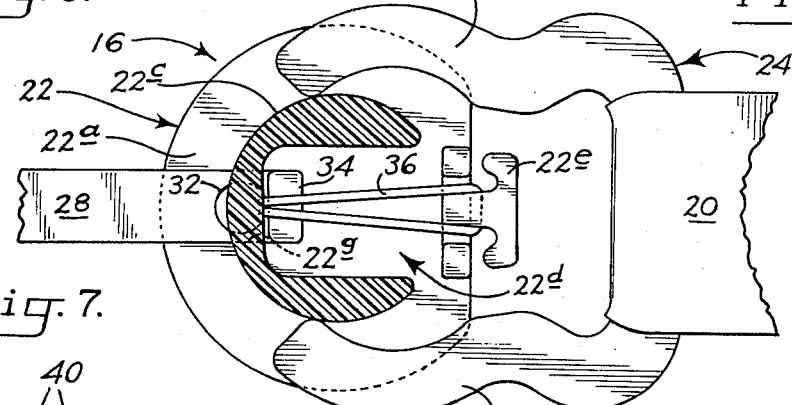
FIG. 7 is similar to FIGS. 5 and 6, and illustrates a releasing action.

Throughout the normal range of tensions permitted by elongation in band 36, the arms in mechanism part 24 remain substantially closely conforming to the outside surface of hub 22d. And, as a consequence, there is no tendency of the release mechanism to release. However, if something occurs which tends to pull the facebow away from the wearer's face, and on enlargement 34 substantially bottoming out against the inside end of slot 22g, arms 24a, 24b begin to slide relative to hub 22c and to separate, so as to change the geometry of part 24 such as is illustrated in FIG. 7. This action occurs smoothly, with separation of arms 24a, 24b contributing to a build-up of tension throughout the assembly. Such build-up extends in a tension range exceeding that afforded by stretching of band 36.

The condition shown in FIG. 7 is one in which the relative positions between parts 22, 24 are just slightly short of a releasing condition. In the event that whatever has pulled the facebow stops this action, and with the parts in the relative positions shown in FIG. 7, the arms and hub interact with a restoring force to return the release mechanism to the condition initially existent. However, when pulling on the facebow exerts a predetermined maximum tension level through mechanisms 22, 24, arms 24a, 24b slip far enough on hub 22c to cause the mechanism to release. When this occurs, obviously no slingshot return is possible in the facebow. The mentioned maximum tension level is determined by resilience in arms 24a, 24b.

When a release takes place, it should be evident that reassembly of parts 22, 24 in a mechanism is an extremely simple thing for a wearer to accomplish. This is done simply by pushing these parts back together, whereupon the arm 24g, 24b separate and again snap into close conforming fitting around hub 22cs. It will further be noted that there is little likelihood that a user of the apparatus can impair or defeat the safety-release opertion just described. Further, it will be noted that through defining a short travel limit between parts 22, 24 which will effect a release, is not possible for a facebow to pulled sufficiently far to cause injury if let go of before a release takes place.

Figure 8:
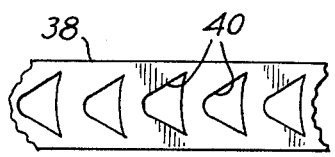
FIG. 8 is a fragmentary side elevation, on about the same scale as FIGS. 4–7, inclusive illustrating a modified form of a connector strap used with the mechanism of the invention.
Figure 9:
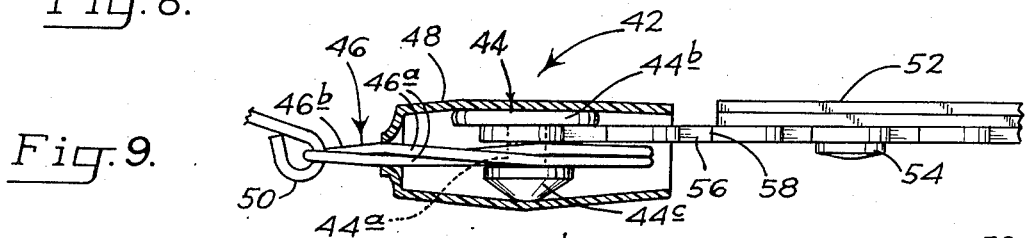
FIG. 9 is a fragmentary top plan view, on about the same scale as FIGS. 2–8, inclusive, illustrating a modified form of the invention.

Considering for a moment several slight modifications of the apparatus so far described, it is appreciated that instead of there being used an elastic band between a web and a tab, coil springs of different selected sizes may be used as well—preferably individually. Further, there may be some instances in which it is desirable to provide a web, such as web 28, with holes having generally triangular or arrowhead shapes such as those illustrated at 38 on a web 40 in FIG. 8. Also, while plastic materials have generally been indicated above for the parts in the mechanism, other materials may also be used.

Referring now to FIGS. 9-12, inclusive, these show an alternate form of a safety-release mechanism also constructed in accordance with the present invention. Only one mechanism is shown in these drawings, such being indicated generally at 42, but it will be appreciated that two mechanisms are used in connection with attaching the opposite outer ends of a facebow with the opposite ends of a neckstrap, or the like, such as is illustrated in FIG. 1. Included in mechanism 42 are mechanism parts 44, 46 which correspond, in function, to parts 22, 24, respectively, in mechanism 16. Part 44 takes the form, generally, of a button, having a reduced cylindrical central portion 44a which joins with opposite enlarged-diameter end portions 44b, 44c having the configurations illustrated. Part 46 takes the form of a specially bent spring-wire unit, also having the configuration clearly illustrated in the figures. So as to protect a wearer from any scratching by part 46, a pliable protective sleeve 48 fits loosely around the mechanism as shown. Part 46 includes a pair of opposed relatively movable arms 46a which, normally, fit around central portion 44a in part 44 as shown. Part 46 is provided with a loop 46b which is intended to be hooked to the outer end of a face bow, such as the outer end shown at 50.

Indicated at 52 is a neckstrap, similar to neckstrap 14, on opposite ends of which are mounted projecting buttons, such as that shown at 54. An elongated web 56 having perforations or openings 58 distributed along its length interconnects button 54 and part 44 as shown.

Figure 10:
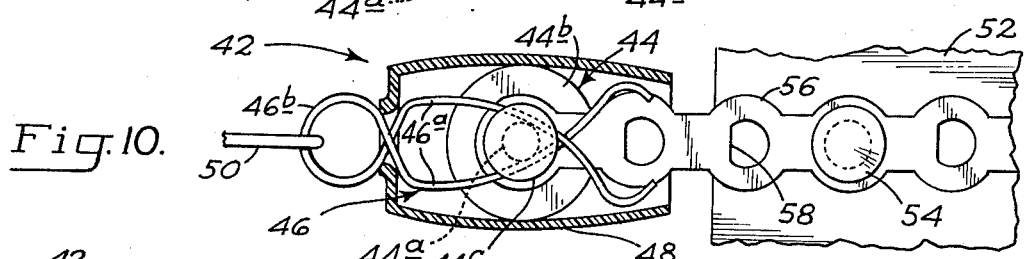
FIG. 10 is a side elevation taken generally from the bottom side of FIG. 9.

When the apparatus of FIGS. 9-12, inclusive, is mounted for use, the orthodontist selects the points of attachments between web 56 and buttons 54. Tension is created through the mechanism by virtue of the action of spring arms 46a on the central portions or parts 44. FIG. 10 illustrates a condition with arms 46a slightly separated from their normal conditions, and hence exerting a tension through the overall assembly.

Figures 11, 12:
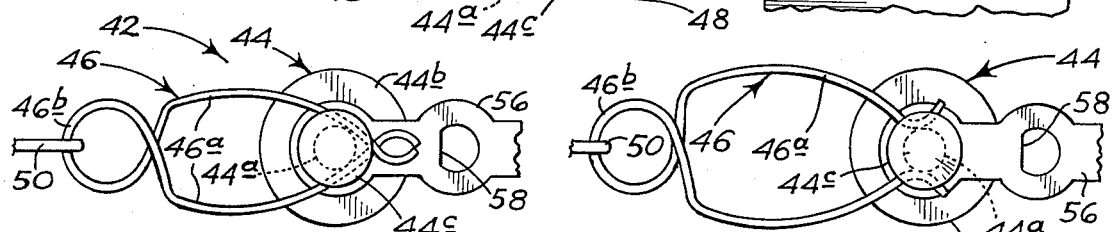
FIGS. 11 and 12 are similar to FIG. 10, and illustrate a releasing action in the mechanism of FIGS. 9 and 10.

Any tendency of any action to pull a facebow away from a wearer's face results in sliding of these arms relative to central portion 44a, with separation of the arms and attendant increasing of tension through the assembly. This kind of condition is illustrated in FIG. 11, slightly short of a releasing action. When, however, the tension level transmitted through the apparatus reaches the predetermined maximum tension level, part 44 escapes between the arms to effect a release. FIG. 12 indicates the situation which exists between the parts substantially at the point of release.

Not only may the desired force level be determined as above-indicated, but also, it is possible to use spring wires of different sizes and curvatures for part 46 to provide a selection of different ranges of tensions.

After a releasing operation, reassembly takes place by slipping sleeves 48 over the outer ends of a facebow, and simply inserting end portions 44c back through the spaces provided and defined between arms 46a. As was the case in the first-described embodiment of the invention, that illustrated in FIGS. 9-12, inclusive, allows for angulation between a facebow and a neckstrap or headstrap.

It is thus apparent that a unique safety-release tension-producing mechanism is offered by the invention. The operating features of the two embodiments of the invention which have been described, and the advantages thereof, have been set forth above. It will further be noted that in each of the embodiments described a relatively simple and low-cost construction is used. In both embodiments it is a simple matter for an orthodontist to select the desired appropriate force to be transmitted, and it is also a simple matter for a wearer to reassemble the mechanisms if and when a release takes place. Positive releasing takes place in all situations prior to a time that a facebow can be pulled sufficiently far to produce a damaging slingshot effect.

Therefore, while a preferred and an alternate embodiment of the invention have been described, it is appreciated that other variations and modifications may be made without departing from the spirit of the invention.

It is claimed and desired to secure by Letters Patent:

1. Safety-release tension-applying mechanism for operative interposition between an end of an orthodontic facebow and an adjacent end of a headstrap and the like for the facebow, said mechanism comprising
    a first mechanism part including an attaching portion having a convex circular surface expanse of revolution including a pair of spaced, generally opposing gripping-surface portions, and
    a second mechanism part including a infinitely changable tension-producing portion having a changable-geometry concave circular surface expanse of revolution including a pair of spaced, generally opposing gripping-surface portions which, through changes in geometry, are complementarily fittable against and releasably engagable with said gripping-surface portions in said convex surface expanse of revolution in said attaching portion in said first part to assist in producing tension in an overall assembly including the release mechanism, headstrap and facebow, said tension-producing portion, when so engaged with said attaching portion, automatically releasing therefrom along a release axis, through changes occurring in its geometry, on the tension transmitted through such an assembly exceeding a predetermined tension level, said two pairs of gripping-surface portions, when engaged, accommodating sliding-contact pivoting about an axis substantially normal to said release axis.

2. The mechanism of claim 1, wherein said tension-producing portion includes a pair of spaced, opposed relatively movable elements which, in a relaxed state, have a preselected normal set of positions relative to one another, said elements being elastically movable relative to one another out of said normal set of positions to assist in producing tension in an assembly including the release mechanism, a facebow and a headstrap.

* * * * *